United States Patent [19]

Horton et al.

[11] Patent Number: 5,382,242
[45] Date of Patent: Jan. 17, 1995

[54] CAPPING DEVICE FOR CONDUIT CONNECTOR

[75] Inventors: Duane L. Horton, St. Louis, Mo.; Richard V. Nye, Laguna Hills, Calif.

[73] Assignee: Mallinckrodt Medical, Inc., St. Louis, Mo.

[21] Appl. No.: 103,014

[22] Filed: Aug. 6, 1993

[51] Int. Cl.6 .................................................. A61M 25/00
[52] U.S. Cl. ................................... 604/283; 604/284; 604/263; 604/905
[58] Field of Search ............... 604/167, 169, 256, 263, 604/280, 283, 284, 326, 905; 215/224, 306, 316, 317, 320, 321, 324, 340, 345

[56] References Cited

U.S. PATENT DOCUMENTS

| | | | |
|---|---|---|---|
| 3,513,849 | 5/1970 | Vaillancourt et al. | 604/283 |
| 3,707,972 | 1/1973 | Villari et al. | |
| 3,741,217 | 6/1973 | Ciarico | |
| 3,814,103 | 6/1974 | Fettel et al. | |
| 4,349,024 | 9/1982 | Ralston, Jr. | 604/905 |
| 4,416,273 | 11/1983 | Grimeo | |
| 4,580,556 | 4/1986 | Kondur | |
| 4,653,477 | 3/1987 | Akui et al. | 604/256 |
| 4,661,110 | 4/1987 | Fortier et al. | |
| 5,017,188 | 5/1991 | Marten et al. | 604/256 |
| 5,092,850 | 3/1992 | Bume | 604/256 |
| 5,263,944 | 11/1993 | Vidal et al. | 604/256 |

Primary Examiner—C. Fred Rosenbaum
Assistant Examiner—Perry E. Van Over
Attorney, Agent, or Firm—David A. Hey

[57] ABSTRACT

A capping device for covering the access port of a conduit connector includes a first cap having a downwardly extending skirt and an access opening through which a bronchoscope, catheter or other small diameter medical device may be inserted. The skirt includes an inwardly extending rim around its internal surface which detachably snaps over a lip around the access port. The access opening is selectively sealable by a second cap that is tethered to the first cap by a flexible tether strap. The second cap also incudes a downwardly extending skirt including an inwardly extending rim around its internal surface which detachably snaps over a lip around the first cap. The capping device further includes a flexible anchor strap extending from the first cap which snaps onto a knob on the connector, thereby retaining the capping device on the connector when not in use.

23 Claims, 2 Drawing Sheets

CAPPING DEVICE FOR CONDUIT CONNECTOR

BACKGROUND

The present invention relates to capping devices for use with medical devices such as endotracheal tubes, endobronchial tubes and connectors therefore.

During continuous mechanical ventilation of patients, a common clinical practice involves the use of Positive End Expiratory Pressure, wherein the ventilator provides a specific amount of pressure during the expiratory phase of ventilation. This "pressure breathing" facilitates ventilating the entire lung system of the patient, and assists the breathing of those with injuries or debilitating illnesses having breathing difficulties. The slight positive pressure of the incoming air during gas assist inhalation must be overcome during expiration, and suitable valves and pressure regulators are placed in the ventilation circuit to allow for expiration.

It is often necessary to have access to a patient's airways during mechanical ventilation. For example, one procedure that is frequently performed is bronchoscopy. Bronchoscopy involves the insertion of a thin instrument, called a bronchoscope, into a patient's airways for visual inspection of the patient's lung and bronchial passages. If access is not provided for in the ventilation system, the patient must be disconnected from the ventilator prior to insertion of the bronchoscope. If access is provided, such access must be sealable when the access is not needed so that the ventilation of the patient may be properly maintained. Further, it is also desirable that even when performing a procedure such as bronchoscopy, that the ventilation system remains sealed around the inserted instrument so as to maintain the ventilation pressure to as high a degree as possible.

There are numerous capping devices with access ports for ventilation tubes and connectors known in the prior art as represented by the following. However, all of the known capping devices suffer from disadvantages as will be discussed below.

U.S. Pat. No. 4,416,273 to Grimes shows a cap valve assembly which has a cap that allows for the admission of a thin tubular instrument while keeping sealed the end of the connector through which the instrument is inserted. However, the Grimes cap suffers from the disadvantage that the only way to fully open the connector is to completely disconnect the cap from the connector, thereby risking loss of the cap.

U.S. Pat. No. 4,580,556 to Kondur discloses a plugged connector cap wherein both the plug and the cap are independently tied to the connector by cords. While the cap cord of Kondur permits removal of the cap from its connector opening without disconnecting the cap from the connector, the cord can not be easily removed from the connector if it is desired to completely disconnect the cap from the connector, such as to replace the cap.

U.S. Pat. No. 3,814,103 to Fettel et al describes a stopper having an integrally formed holding strap for engaging a connector. This construction also allows for removal of the stopper without total disconnection from the connector, however, total removal of the stopper and holding strap is difficult. Also, this device does not provide for maintenance of maximum ventilation pressure when the stopper is in an open position.

U.S. Pat. No. 3,707,972 to Vallari et al shows a plug for one arm of a two channel irrigation system connector. The plug is permanently attached to the arm by a tether strap.

U.S. Pat. No. 3,741,217 to Clarico also describes a plug for one side arm of an irrigation system connector. This plug includes a tether strap with an attachment ring which circles the connector when in use. This keeps the plug attached to the connector when the plug is not engaged in the side arm opening, but total removal from the connector is difficult.

U.S. Pat. No. 4,661,110 to Fortier et al discloses a connector fitting of medical tubes having various plug adaptions for closing coupling elements which may be attached to the medical tube. The connector fitting of Fortier et al is tethered to the medical tube by a coupling ring, which makes removal from the tube difficult.

As seen above, the devices known from the prior art all have disadvantages. Further, none of the prior art capping devices are specifically designed to allow insertion of instruments into a ventilation tube while maintaining the maximum ventilating pressure. In addition, it is desirable to overcome other disadvantages related to the loss of ventilation pressure, such as by inadvertent displacement of the plug portion of the capping device.

Accordingly, there remains a need in the art for improvements in capping devices for covering openings in conduit connectors.

Objects Of The Invention

It is one object of the present invention to provide a capping device for a conduit connector of a ventilation tube, the capping device allowing easy access for the insertion of various devices into the ventilation tube while maintaining a maximum ventilating pressure.

It is another object of the present invention to provide a capping device as described above, wherein the capping device includes a plug portion, such plug tightly sealing the access opening when access is not needed.

It is a further object of the present invention to provide a capping device as described above, wherein the plug can not easily be displaced through inadvertent movement or disturbance, but which can be easily removed upon need for access to the access opening of the ventilation tube.

SUMMARY OF THE INVENTION

The present invention provides a capping device for covering the mouth of an access port of a conduit connector and a combination of such a capping device with a conduit connector. The capping device includes a first cap having a downwardly extending skirt and an access opening through which a bronchoscope, catheter or other small diameter medical device may be inserted. The access opening is surrounded by a sealing membrane which seals around the periphery of an instrument inserted through the access opening to enable maintenance of ventilation pressure. The skirt includes an inwardly extending rim around its internal surface which detachably snaps over a lip around the mouth of the access port of the conduit connector. The access opening of the first cap is selectively sealable by a complementary second cap which snap fits over the upper portion of the first cap and which is tethered to the first cap by a flexible tether strap. The second cap includes a plug fitting extending from the center of the lower side thereof which securely seals the access opening of the first cap when the second cap is engaged over the first cap. The capping device further includes a flexible anchor strap extending from the cap which snaps onto a knob on the conduit connector, thereby retaining the cap on the connector when not covering the mouth of the access port.

DETAILED DESCRIPTION OF THE INVENTION

Figure 1:
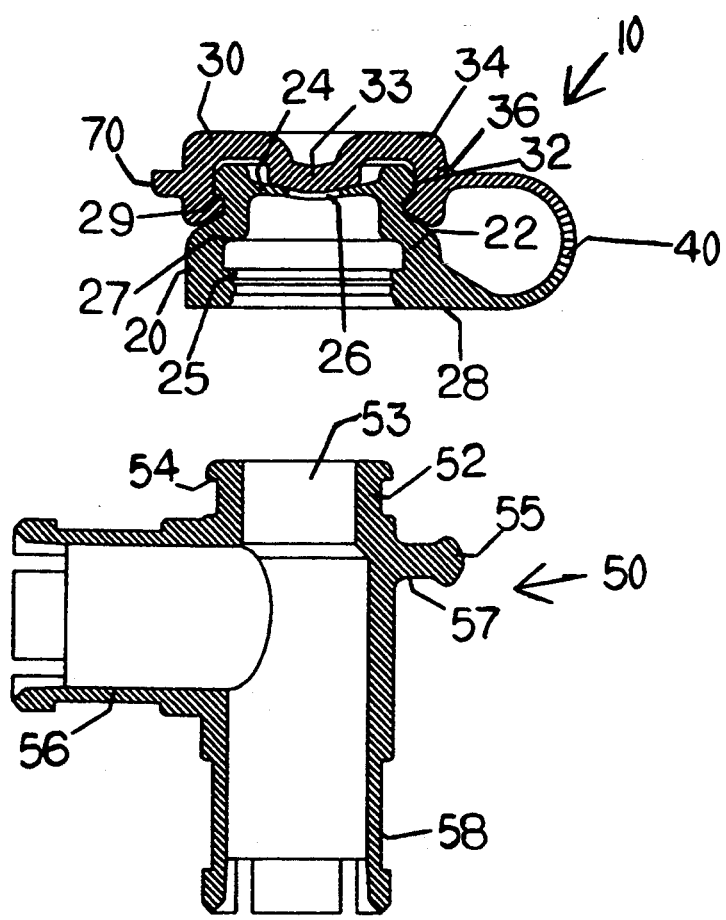
FIG. 1 is an exploded, cross sectional view of the capping device and connector, according to one embodiment of the present invention, the capping device 10 being shown in a closed position.
Figure 2:
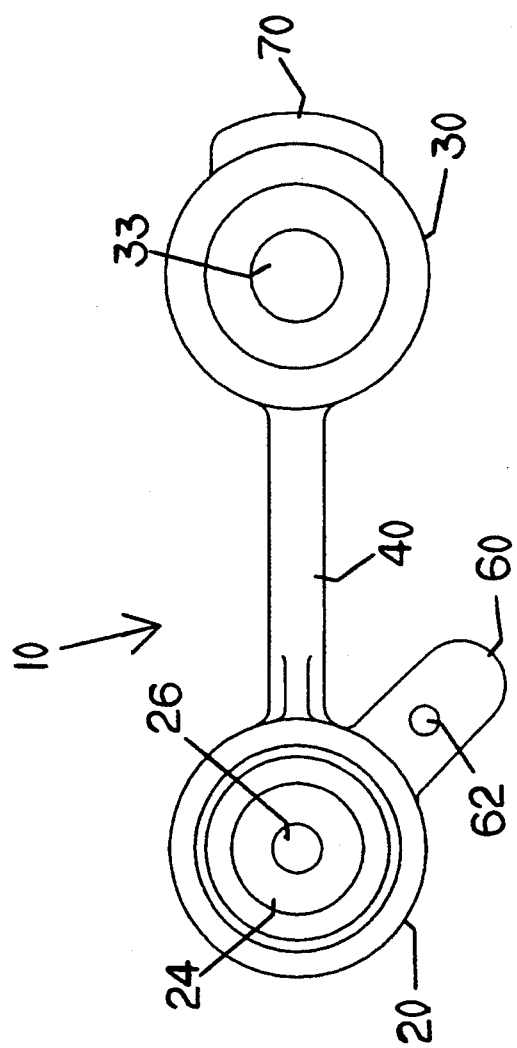
FIG. 2 is top plan view of the capping device according to the present invention, the capping device being shown in an open position.

Referring now to FIGS. 1 and 2, wherein like Darts are designated by like reference numerals, there is shown a capping device, generally designated by reference numeral 10, which includes a first cap 20, and a second cap 30, tethered to the first cap 20, by a tether strap 40.

The first cap 20, includes a cover portion 22, which extends toward the center of the first cap, and also includes a membrane 24, and an access opening 26, which are sized and act in concert to provide a substantially airtight fit with the body of examining instruments, such as a bronchoscope (not shown), which may be inserted through the access opening 26. A continuous skirt 28, extends downwardly from the cover portion 22. In the embodiment shown, the capping device 10, is made in one piece of a soft elastomeric material, such as silicone rubber or thermoplastic elastomer.

A connector, generally designated by reference numeral 50, which is shown as being generally T-shaped, has three inlets 52, 56, and 58, to a common passageway within connector 50. An access port 53, which provides access to inlet 52, may be selectively closed by snap-engaging the capping device 10, thereover. The capping device 10, is snapped in place on the connector 50, by the engagement of the first cap 20, over a lip 54, of the inlet 52. A sealing fit between the first cap 20, and the inlet 52, is achieved by interaction of a first interior rim 25, of the first cap 20, and the lip 54, of inlet 52. A second interior rim 27, parallel to the first rim 25, is provided on the first cap 20, to improve sealing of the first cap 20, over inlet 52.

To assure that the capping device 10, will remain anchored to the connector 50, when not covering the access port 53, the connector 50, includes a knob 55, conveniently located adjacent the inlet 52. The capping device 10, includes as anchor strap 60, which extends from the first cap 20. The anchor strap 60, has a keeper opening 62, which may be snapped over the knob 55, on the connector 50, to anchor the capping device 10, to the connector 50, The knob 55, extends outwardly of inlet 52, by means of a neck 57. The diameter of the keeper opening 62, is smaller than the diameter of the knob 55, and this enables the anchor strap 60, to be retained on the neck 57, after the anchor strap 60, is snapped over the knob 55. When the capping device 10, is not sealing access port 53, the neck 57, allows the capping device 10, to be easily rotated out the way of the inlet 52, for performing a medical procedure through the access port 53. As best seen in FIG. 2, the width of the anchor strap 60, is greater than the width of the tether strap 40, thereby making the anchor strap 60, less flexible and less subject to twisting than the tether strap 40. This facilitates rotation of anchor strap 60, about neck 57. Further, for ease of operation, the anchor strap 60, is made shorter than the tether strap 40, thereby preventing the capping device 10, from flopping about while it is anchored to the connector 50, by anchor strap 60, alone.

The second cap 30, includes a cover portion 34, which comprises a upper portion of the second cap 30. A continuous skirt 36, extends downwardly from the cover portion 34. In addition, the second cap 30, includes a plug fitting 33, provided on the lower surface of the cover portion 34.

The second cap 30, may be snapped in place over the first cap 20, to completely seal the access opening 26. A sealing fit between the second cap 30, and the first cap 20, is achieved by interaction of an interior rim 32, of the second cap 30, and a lip 29, of the first cap 20. In addition, the plug fitting 33, acts to completely seal the access opening 26, of the first cap 20, when the second cap 30, is snap engaged with the first cap 20. A good seal of the access opening 26, is assured by dimensioning the plug fitting 33, to have a diameter slightly larger than the diameter of the access opening 26, and to have a depth slightly greater than the distance between the lower surface of the second cap 30, and the upper surface of the membrane 24, of the first cap 20, when the second cap 30, is engaged over the first cap 20. In this way, the plug fitting 33, will completely cover the access opening 26, and will exert a slight pressure on the membrane 24, to effectively seal the access opening 26, when the second cap 30, is engaged with the first cap 20. A pull tab 70, may be provided on the second cap 30, to allow the second cap 30, to be more easily removed from the first cap 20.

It is important to note the double sealing arrangement provided between the second cap 30, and first cap 20, according to the present invention. In particular, the snap engagement of the interior rim 32, of the second cap 30, and the lip 29, of the first cap 20, provides an airtight reliable seal around the periphery of first cap 20. However, as previously noted, the plug of several prior art devices can become easily displaced from the access opening because of inadvertent movement or disturbance. In addition, the plug of several prior art devices does not seal the access opening in an airtight manner, but rather allows air to escape from the area between the plug and the periphery of the access opening. The capping device according to the present invention overcomes all of these disadvantages and still allows for easy access to the access opening when desired. In particular, the interaction of plug fitting 33, of second cap 30, with the membrane 24, or first cap 20, provides a reliable and airtight seal for the access opening 26, when the second cap 30, is engaged over first cap 20.

The double seal arrangement of the present invention provides several advantages. In particular, the double seal provides a reliable, airtight seal, and is instrumental in maintaining a secure closure against inadvertent displacement of the second cap 30, from the first cap 20. Further, the double seal of the present invention prevents leakage problems that can lead to reduction or loss of system pressure.

While the connector shown in the FIG. 1, is a generally T-shaped connector, it is understood that other types of connectors, such as Y-shaped connectors, and straight connectors may also be used with the capping device of the present invention.

When a patient is on mechanical ventilation, it may be desirable to pass an examining instrument such as a bronchoscope (not shown) into the patient's airways for visual examination thereof. Also, a patient on mechanical ventilation may require frequent suctioning through a suction catheter (not shown) to maintain proper bronchial hygiene. Both the bronchoscope and catheter are long, slender, tubular devices that may be inserted through the endotracheal tube connector and endotracheal tube when in place. A bronchoscope, catheter or other slender instrument of suitable diameter may be inserted through the access opening 26, of the first cap 20. Preferably, the access opening 26, is about 3 to 4 mm (0.14 to 0.15 in) in diameter and the resilience of the membrane 24, allows the access opening 26, to stretch to accommodate instruments up to about 8 mm in diameter. When a suitably sized instrument is inserted through the access opening 26, the membrane 24, squeezes about the inserted instrument, sealing the access opening 26, against loss of ventilation pressure. Thus, by using the capping device according to the present invention, it is possible to maintain positive system pressure even while a suitably sized bronchoscope or catheter is present within access opening 26, of first cap 20. When the instrument is removed, the second cap 30, may be quickly snapped over the first cap 20, to reseal the access opening 26.

In certain instances, such as for suctioning procedures which do not require that the access port 53, be airtight, or when an opening larger than that provided by the access opening 26, is needed, the first cap 20, may be removed from the inlet 52, of the connector 50. Because the first cap 20, is flexible, it is readily released by unsnapping the skirt 28, from its position over the lip 54, of the inlet 52. Once the first cap 20, is disengaged from the inlet 52, a suctioning catheter or other instrument may be inserted directly through the access port 53.

Because the capping device 10, remains attached to the connector 50, by the anchor strap 60, the capping device 10, is retained just out of the way of the procedure being performed so that it may be quickly replaced over the inlet 52, at the end of the procedure by snapping the skirt 28, over the lip 54, of the inlet 52. Also, the capping device 10, can be completely snap-disengaged from the connector 50, if desired, such as for cap replacement. This can be carried out quickly and easily without disassembly of the ventilation tubing, as is required with some prior art devices.

The present invention provides a convenient-to-use capping device for covering a conduit connector access opening of a ventilating device. The capping device of the invention permits selective access through a selectively closable access opening for complementarily sized instruments. For access with larger size instruments, or when an airtight seal is not needed, the cap can be snap-disengaged from the access port of the conduit connector and rotated completely out of the way of the access port, while remaining anchored to the conduit connector by a separately snap-engageable anchor strap.

The capping device according to the present invention provides several advantages over prior art capping devices. In particular, the capping device of the present invention, provides means of allowing easy access for insertion of various devices into a ventilation tube while maintaining the maximum system pressure. In addition, the capping device according to the present invention, may be completely removed from the access port of the ventilation tube, but the capping device remains readily accessible for reclosure of the access port, by means of a flexible tether strap. In the alternative, the capping device according to the present invention, can be easily disconnected entirely from the ventilation tube when so desired.

The foregoing has been a description of certain preferred embodiments of the present invention, but is not intended to limit the invention in any way. Rather, many modifications, variations and changes in details may be made within the scope of the present invention.

What is claimed is:

1. A combination of a conduit connector and a capping device; the conduit connector having three inlets leading to a common passageway within said conduit connector, one of said inlets comprising an access port for providing access from outside said conduit connector to said common passageway;

and the capping device comprising:

a first cap for covering and sealing said access port of said conduit connector; the first cap having an access opening therethrough which allows access to said common passageway within said conduit connector without removing said first cap from said conduit connector; wherein said first cap is selectively removable form said conduit connector;

a second cap for selectively sealing said access opening of said first cap;

a flexible tether strap connecting said second cap with said first cap; and a flexible anchor strap extending from said first cap; said anchor strap having means at one end for detachably snap-engaging said anchor strap with said conduit connector to selectively anchor said capping device to said conduit connector;

wherein said conduit connector includes a first lip extending peripherally outward from said access port of said conduit connector; and wherein said first cap includes:

a first cover portion for extending across said access port of said conduit connector; and a first continuous skirt portion extending from said first cover portion and terminating in a first inwardly projecting rim; said first rim being detachably snap-engageable with said first lip of said access port of said conduit connector to form a sealing fit between said first cap and said conduit connector.

2. A combination according to claim 1, wherein said conduit connector further includes an outwardly projecting knob to which said anchor strap is detachably snap-engageable.

3. A combination according to claim 2, wherein said knob includes an enlarged head portion which is connected to said conduit connector by a neck member; and wherein said anchor strap is rotatable perpendicularly about said neck member when said anchor strap is snap-engaged with said knob.

4. A combination according to claim 3, wherein said snap-engaging means of said anchor strap comprises a keeper opening having a diameter smaller than the diameter of said head portion of said knob.

5. A combination according to claim 2, wherein said knob is adjacent said access port.

6. A combination according to claim 1, wherein said first cap includes a second lip extending peripherally outward from said first cover portion; and wherein said second cap includes:

a second cover portion comprising an upper portion of said second cap;

a second continuous skirt portion extending from said second cover portion and terminating in a third inwardly projecting rim; said third rim being detachably snap-engageable with said second lip of said first cap to form a sealing fit between said second cap and said first cap; and a plug fitting provided on the lower surface of said second cover portion.

7. A capping device according to claim 6, wherein said plug fitting has a diameter larger than the diameter of said access opening; and has a depth slightly greater than the distance between the lower surface of said second cover portion of said second cap and the upper surface of said membrane of said first cap, when said second cap is engaged with said first cap.

8. A combination according to claim 1, wherein said first skirt portion of said first cap includes a second inwardly projecting rim that is parallel with said first rim; said second rim extending around the internal surface of said first skirt portion and being spaced away from said first cover portion; said second rim further providing a sealing fit between said first cap and said conduit connector.

9. A combination according to claim 1, wherein said capping device is formed in one-piece of a flexible material.

10. A combination according to claim 1, wherein said anchor strap is substantially shorter than said tether strap.

11. A combination according to claim 1, wherein said anchor strap is less flexible than said tether strap.

12. A combination according to claim 1, wherein said conduit connector is T-shaped.

13. A combination according to claim 1, wherein said second cap further includes a pull tab.

14. A combination according to claim 1, wherein said access opening is about 3-4 mm in diameter.

15. A capping device for covering an access port of a conduit connector;

wherein said conduit connector includes a first lip extending peripherally outward from said access port, and further includes an outwardly projecting knob;

the capping device comprising:

a first cap for selectively sealing said access port of said conduit connector, said first cap having a first cover portion for extending across said access port of said conduit connector, said first cover portion having an access opening extending therethrough which allows access to inside said conduit connector without removing said first cap from said conduit connector;

a first continuous skirt portion extending from said first cover portion, said first skirt portion having a first inwardly projecting rim which extends around an internal surface of said first skirt portion and which is spaced away from said first cover portion, wherein said first rim is detachably snap-engageable with said first lip of said conduit connector to form a sealing fit between said first cap and said conduit connector; and a second lip extending peripherally outward form said first cover portion;

a second cap for selectively sealing said access opening of said first cover portion of said first cap; said second cap having a second cover portion comprising an upper portion of said second cap;

a second continuous skirt portion extending from said second cover portion, said second skirt portion having a second inwardly projecting rim which extends around an internal surface of said second skirt portion and which is spaced away from said second cover portion, wherein said second rim is detachably snap-engageable with said second lip of said first cap to form a sealing fit between said second cap and said first cap; and a plug fitting provided on the lower surface of said second cover portion;

a flexible tether strap connecting said first cap with said second cap; and a flexible anchor strap extending from said first cap, said anchor strap having means at one end for detachably snap-engaging said anchor strap with said knob of said conduit connector to selectively anchor said capping device to said conduit connector;

wherein said first skirt portion of said first cap includes a third inwardly projecting rim that is parallel with said first rim, said third rim extending around the internal surface of said first skirt portion and being spaced away from said first cover portion; said third rim further providing a sealing fit between said first cap and aid conduit connector.

16. A capping device according to claim 15, wherein said capping device is formed in one-piece of a flexible material.

17. A capping device according to claim 15, wherein said knob is adjacent said access port of said conduit connector.

18. A capping device according to claim 15, wherein said anchor strap is substantially shorter than said tether strap.

19. A capping device according to claim 15, wherein said anchor strap is less flexible than said tether strap.

20. A capping device according to claim 15, wherein said second cap further includes a pull tab.

21. A capping device according to claim 15, wherein said access opening is about 3-4 mm in diameter.

22. A capping device for covering an access port of a conduit connector;

wherein said conduit connector includes a first lip extending peripherally outward from said access port, and further includes an outwardly projecting knob;

the capping device comprising:

a first cap for selectively sealing said access port of said conduit connector, said first cap having a first cover portion for extending across said access port of said conduit connector, said first cover portion having an access opening extending therethrough which allows access to inside said conduit connector without removing said first cap from said conduit connector;

a first continuous skirt portion extending form said first cover portion, said first skirt portion having a first inwardly projecting rim which extends around an internal surface of said first skirt portion and which is spaced away from said first cover portion, wherein said first rim is detachably snap-engageable with said first lip of said conduit connector to form a sealing fit between said first cap and said conduit connector; and a second lip extending peripherally outward from said first cover portion;

a second cap for selectively sealing said access opening of said first cover portion of said first cap; said second cap having a second cover portion comprising an upper portion of said second cap;

a second continuous skirt portion extending from said second cover portion, said second skirt portion having a second inwardly projecting rim which extends around an internal surface of said second skirt portion and which is spaced away from said second cover portion, wherein said second rim is detachably snap-engageable with said second lip of said first cap to form a sealing fit between said second cap and said first cap; and a plug fitting provided on the lower surface of said second cover portion;

a flexible tether strap connecting said first cap with said second cap; and a flexible anchor strap extending from said first cap, said anchor strap having means at one end for detachably snap-engaging said anchor strap with said knob of said conduit connector to selectively anchor said capping device to said conduit connector wherein said knob includes an enlarged head portion which is connected to said conduit connector by a neck member; and wherein said anchor strap is rotatable perpendicularly about said neck member when said anchor strap is snap-engaged with said knob; and wherein said snap-engaging means of said anchor strap comprises a keeper opening having a diameter smaller than the diameter of said head portion of said knob.

23. A capping device for covering an access port of a conduit connector;

wherein said conduit connector includes a first lip extending peripherally outward from said access port, and further includes an outwardly projecting knob;

the capping device comprising:

a first cap for selectively sealing said access port of said conduit connector, said first cap having a first cover portion for extending across said access port of said conduit connector, said first cover portion having an access opening extending therethrough which allows access to inside said conduit connector without removing said first cap from said conduit connector;

a first continuous skirt portion extending form said first cover portion, said first skirt portion having a first inwardly projecting rim which extends around an internal surface of said first skirt portion and which is spaced away from said first cover portion, wherein said first rim is detachably snap-engageable with said first lip of said conduit connector to form a sealing fit between said first cap and said conduit connector; and a second lip extending peripherally outward from said first cover portion;

a second cap for selectively sealing said access opening of said first cover portion of said first cap; said second cap having a second cover portion comprising an upper portion of said second cap;

a second continuous skirt portion extending from said second cover portion, said second skirt portion having a second inwardly projecting rim which extends around an internal surface of said second skirt portion and which is spaced away from said second cover portion, wherein said second rim is detachably snap-engageable with said second lip of said first cap to form a sealing fit between said second cap and said first cap; and a plug fitting provided on the lower surface of said second cover portion;

a flexible tether strap connecting said first cap with said second cap; and a flexible anchor strap extending from said first cap, said anchor strap having means at one end for detachably snap-engaging said anchor strap with said knob of said conduit connector to selectively anchor said capping device to said conduit connector;

wherein said plug fitting has a diameter larger than the diameter of said access opening; and has a depth slightly greater than the distance between the lower surface of said second cover portion of said second cap and the upper surface of said membrane of said first cap, when said second cap is engaged with said first cap.

* * * * *